US00PP37189P2

(12) United States Plant Patent
van Diepen

(10) Patent No.: US PP37,189 P2
(45) Date of Patent: Jan. 6, 2026

(54) ***HELLEBORUS* PLANT NAMED 'Flevo 20-11-101'**

(50) Latin Name: ***Helleborus* x *ericsmithii* X *Helleborus* x *hybridus***
Varietal Denomination: Flevo 20-11-101

(71) Applicant: FlevoFlora B.V., Marknesse (NL)

(72) Inventor: Theodorus L. M. van Diepen, Marknesse (NL)

(73) Assignee: FLEVOFLORA B.V., Marknesse (NL)

( * ) Notice: Subject to any disclaimer, the term of this patent is extended or adjusted under 35 U.S.C. 154(b) by 0 days.

(21) Appl. No.: 19/224,782

(22) Filed: May 31, 2025

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

(56) References Cited

U.S. PATENT DOCUMENTS

PP28,008 P3 * 5/2017 Davey ..... Plt./439

* cited by examiner

*Primary Examiner* — Susan McCormick Ewoldt
(74) *Attorney, Agent, or Firm* — C. Anne Whealy

(57) ABSTRACT

A new and distinct cultivar of *Helleborus* plant named 'Flevo 20-11-101', characterized by its upright and mounding plant habit; relatively vigorous growth habit; dark green-colored leaves; freely flowering habit; greenish white-colored flower sepals with purplish-tinged margins; and good garden performance.

2 Drawing Sheets

Figure 1:
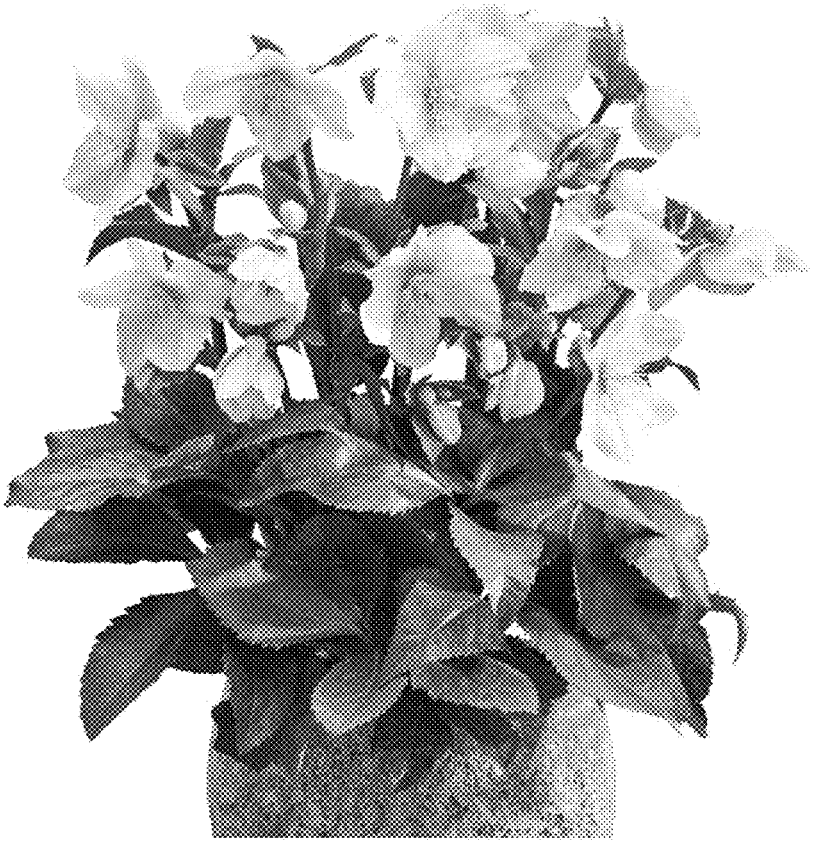

Botanical designation: *Helleborus* x *ericsmithii* X *Helleborus* x *hybridus*.
Cultivar denomination: 'FLEVO 20-11-101'.

CROSS-REFERENCED TO CLOSELY-RELATED APPLICATIONS

A European Community Plant Breeder's Rights application for the instant plant was filed by the Applicant/Assignee of the instant application, FlevoFlora B.V. of Marknesse, The Netherlands on Sep. 30, 2024, application number 2024/2291. Foreign priority is not claimed to this European Community Plant Breeder's Rights application.

BACKGROUND OF THE INVENTION

The present invention relates to a new and distinct cultivar of *Helleborus* plant, botanically known as *Helleborus* x *ericsmithii* X *Helleborus* x *hybridus*, commonly referred to as an interspecific hybrid Hellebore and hereinafter referred to by the name 'Flevo 20-11-101'.

The new *Helleborus* plant is a product of a planned breeding program conducted by the Inventor in Marknesse, The Netherlands. The objective of the breeding program was to create new uniformly mounding and freely-flowering *Helleborus* plants with attractive leaves and flowers.

The new *Helleborus* plant originated from a cross-pollination conducted by the Inventor in Marknesse, The Netherlands in December 2020 of a proprietary selection of *Helleborus* x *ericsmithii* identified as code number 1657VD, not patented, as the female, or seed, parent with an unidentified proprietary selection of *Helleborus* x *hybridus*, not patented, as the male, or pollen, parent. The new *Helleborus* plant was discovered and selected by the Inventor as a single flowering plant from within the progeny of the stated cross-pollination grown in a controlled greenhouse environment in Marknesse, The Netherlands in January 2023.

Asexual reproduction of the new *Helleborus* plant by in vitro meristem culture in a controlled greenhouse environment in Marknesse, The Netherlands since May 2023, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'Flevo 20-11-101'. These characteristics in combination distinguish 'Flevo 20-11-101' as a new and distinct *Helleborus* plant:

1. Upright and mounding plant habit.
2. Relatively vigorous growth habit.
3. Dark green-colored leaves.
4. Freely flowering habit.
5. Greenish white-colored flower sepals with purplish-tinged margins.
6. Good garden performance.

Plants of the new *Helleborus* differ primarily from plants of the female parent selection in the following characteristics:

1. Plants of the new *Helleborus* flower later than plants of the female parent selection.

2. Plants of the new *Helleborus* have larger flowers than plants of the female parent selection.
3. Flower sepals of plants of the new *Helleborus* are greenish white in color with purplish-tinged margin whereas flower sepals of plants of female parent selection are green in color.

Plants of the new *Helleborus* can be compared to plants of *Helleborus* x *hybridus* 'EPB 25', disclosed in U.S. Plant Pat. No. 28,008. In side-by-side comparisons, plants of the new *Helleborus* differ from plants of 'EPB 25' in the following characteristics:

1. Leaflets of plants of the new *Helleborus* have less distinct venation than leaflets of plants of 'EPB 25'.
2. Plants of the new *Helleborus* are more freely branching than plants of 'EPB 25'.
3. Plants of the new *Helleborus* are more freely flowering than plants of 'EPB 25'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'Flevo 20-11-101' grown in a container.

Figure 2:
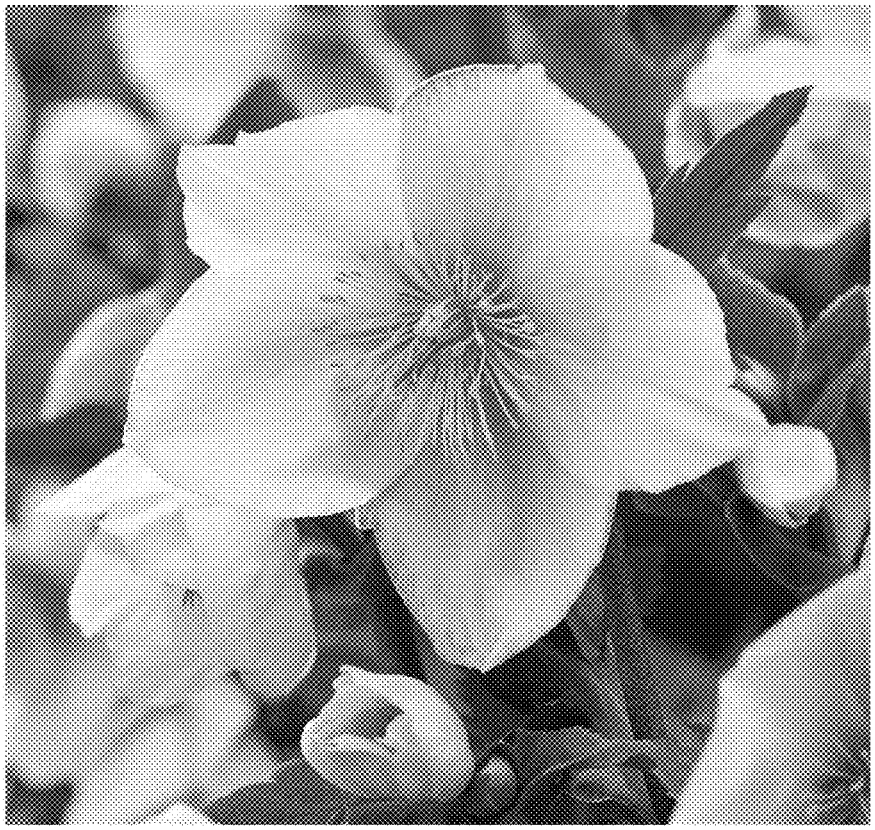

The photograph on the second sheet (FIG. 2) is a close-up view of a typical flowering plant of 'Flevo 20-11-101'.

DETAILED BOTANICAL DESCRIPTION

The aforementioned photographs and following observations, measurements and values describe plants grown in 19-cm containers during the winter in a glass-covered greenhouse in Marknesse, The Netherlands and under cultural practices typical of commercial *Helleborus* production. During the production of the plants, day temperatures ranged from 12° C. to 31° C. and night temperatures ranged from 3° C. to 16° C. Plants were one year old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'Flevo 20-11-101'.

Parentage:

*Female, or seed, parent*.—Proprietary selection of *Helleborus* x *ericsmithii* identified as code number 1657VD, not patented.

*Male, or pollen, parent*.—Unidentified proprietary selection of *Helleborus* x *hybridus*, not patented.

Propagation:

*Type*.—By in vitro meristem culture.

*Time to initiate roots, winter*.—About 52 days at temperatures about 12° C.

*Time to produce a rooted young plant, winter*.—About 20 weeks at temperatures about 2° C. to 14° C.

*Root description*.—Fleshy, variable in thickness; typically white to greenish brown in color, actual color of the roots is dependent on substrate composition, water quality, fertilizer type and formulation, substrate temperature and physiological age of roots.

*Rooting habit*.—Not freely branching; sparse.

Plant description:

*Plant and growth habit*.—Herbaceous perennial; upright and mounding plant habit; overall plant shape, roughly flattened globular; relatively vigorous growth habit and moderate growth rate; leaves arranged in basal rosettes; flowers held within and above the foliar plane.

*Plant height, soil level to top of foliar plane*.—About 28.6 cm.

*Plant height, soil level to top of floral plane*.—About 30.3 cm.

*Plant diameter* (*area of spread*).—About 26.8 cm.

Leaf description:

*Arrangement*.—Leaves arranged alternately in a basal rosette; leaves palmately compound with typically five leaflets per leaf.

*Leaf length*.—About 19.4 cm.

*Leaf width*.—About 24.3 cm.

*Leaflet length*.—About 10.4 cm.

*Leaflet width*.—About 7.1 cm.

*Leaf shape*.—Palmately compound; roughly reniform in outline.

*Leaflet shape*.—Ovate.

*Leaflet apex*.—Acute.

*Leaflet base*.—Attenuate.

*Leaflet margin*.—Dentate; slightly undulate.

*Leaflet texture and luster, upper and lower surfaces*.—Smooth, glabrous; leathery; glossy.

*Leaflet venation pattern*.—Pinnate.

*Leaflet color*.—Developing leaflets, upper surface: Close to 147A; venation, close to 147B. Developing leaflets, lower surface: Close to N148A; midvein, close to 183A. Fully expanded leaflets, upper surface: Close to 147A; venation, close to 143A. Fully expanded leaflets, lower surface: Close to 147B; venation, close to N189A.

*Petioles*.—Length: About 14.9 cm. Diameter: About 6 mm to 7 mm. Texture, upper and lower surfaces: Smooth, glabrous. Color, upper surface: Close to 142A and towards the base, close to N186D; densely covered with fine dots, close to N186D. Color, lower surface: Close to 144A and towards the base, close to N186D; densely covered with fine dots, close to N186D.

Flower description:

*Flower shape and habit*.—Single rotate cyanthiform flowers arranged in loosely-branched terminal and axillary cymes; freely flowering habit with typically about three to four flowers developing per cyme and about 126 flowers developing during the first flowering season; flowers face outwardly to nodding.

*Fragrance*.—None detected.

*Natural flowering season*.—Plants begin flowering about nine months after planting young plants; flower continuously from January to April in The Netherlands.

*Flower longevity on the plant*.—About eleven days; sepals are persistent and other flower parts are not persistent.

Flower buds.—Length: About 2.7 cm. Diameter: About 1.3 cm. Shape: Broadly ovoid. Texture and luster: Smooth, glabrous; matte. Color: Close to 186D.

*Inflorescence height*.—About 24.8 cm.

*Inflorescence diameter*.—About 19.4 cm.

*Flower diameter*.—About 9.3 cm.

*Flower depth* (*height*).—About 2.2 cm.

*Petals*.—None observed; transformed into nectaries.

*Sepals*.—Quantity and arrangement: About five arranged in a single whorl. Length: About 3.7 cm to 5 cm. Width: About 4.5 cm. Shape: Broadly ovate. Apex: Obtuse. Base: Cuneate. Margin: Entire; slightly undulate. Texture and luster, upper surface: Smooth, glabrous; matte. Texture and luster, lower surface: Smooth, glabrous; glossy. Color: When opening, upper surface: Close to 145D; towards the margins, tinged with close to 155D. When opening, lower surface: Close to 145D; towards the margins, tinged with close to 155D; when exposed to light, margins closer to 70C to 70D. Fully opened, upper surface: Close to 145B; towards the margins, tinged with close to N155D with stripes, close to 76C; color becoming closer to 145C with marginal edges, close to N78D, with subsequent development. Fully opened, lower surface: Close to 149D; towards the margins, tinged with close to 70C and occasionally, close to 155D; color becoming closer to 180C with spots, close to 145B, with subsequent development.

*Peduncles*.—Length: About 20.2 cm. Diameter: About 5 mm to 10 mm. Texture and luster: Smooth, glabrous; moderately glossy. Color: Close to 175A flushed with close to N187B with fine dots, close to N187C.

*Pedicels*.—Length: About 2.3 cm to 6.3 cm. Diameter: About 4 mm. Texture and luster: Smooth, glabrous; moderately glossy. Color: Close to N187C with fine dots, close to 143A.

*Reproductive organs*.—Stamens: Quantity per flower: About 110.Filament length: About 1.7 cm. Filament color: Close to 144A; distally, close to 155D. Anther shape: Reniform; basifixed. Anther size: About 2 mm by 3 mm. Anther color: Close to 3C. Pollen amount: Scarce. Pollen color: Close to 4C. Pistils: Quantity per flower: About five. Pistil length: About 1.1 cm. Stigma diameter: About 0.2 mm. Stigma shape: Club-shaped. Stigma color: Close to 143C. Style length: About 1.2 cm. Style color: Close to N187D. Ovary color: Close to 187B.

*Nectaries*.—Quantity per flower: About twelve. Length: About 1 cm. Width: About 3.3 mm. Shape: Tubular, flattened. Texture and luster, inner and outer surfaces: Smooth, glaucous; matte. Color: When opening, inner and outer surfaces: Close to 145A. Fully opened, inner and outer surfaces: Close to N144D and distally, close to N144B; color becoming close to 143D entirely with subsequent development. Seeds and fruits: To date, seed and fruit development have not been observed on plants of the new *Helleborus*.

Garden performance & temperature tolerance: Plants of the new *Helleborus* have been observed to have good garden performance and to tolerate rain and wind. Plants of the new *Helleborus* are suitable for USDA Hardiness Zones 4 to 9 and have been observed to tolerate high temperatures about 34° C.

Pathogen & pest resistance: To date, plants of the new *Helleborus* have not been observed to be resistant to pathogens and pests common to *Helleborus* plants.

It is claimed:

1. A new and distinct *Helleborus* plant named 'Flevo 20-11-101' as herein illustrated and described.

* * * * *